United States Patent [19]

Kuhn et al.

[11] Patent Number: 5,280,021
[45] Date of Patent: Jan. 18, 1994

[54] METHOD AND COMPOSITION FOR THE CONTROL OF PHYTOPATHOGENIC FUNGI

[75] Inventors: David G. Kuhn, Newtown, Pa.; Venkataraman Kameswaran, Princeton Junction, N.J.

[73] Assignee: American Cyanamid Company, Wayne, N.J.

[21] Appl. No.: 803,295

[22] Filed: Dec. 4, 1991

[51] Int. Cl.$^5$ .................... A01N 43/36; A01N 57/00
[52] U.S. Cl. ...................... 514/91; 514/426; 514/427
[58] Field of Search ................ 514/91, 427, 426

[56] References Cited

U.S. PATENT DOCUMENTS

| | | | |
|---|---|---|---|
| 4,929,634 | 5/1990 | Herman et al. | 514/424 |
| 5,010,098 | 4/1991 | Brown et al. | 514/426 |

*Primary Examiner*—Allen J. Robinson
*Attorney, Agent, or Firm*—Michael P. Morris

[57] ABSTRACT

There is provided a method for the prevention and control of fungus infestation of a plant which comprises contacting the fungus or plant, or the soil or water in which the plant is growing, with a 1-(substituted)thioalkylpyrrole compound of formula I

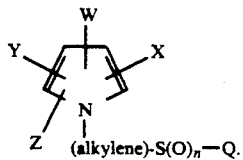

6 Claims, No Drawings

METHOD AND COMPOSITION FOR THE CONTROL OF PHYTOPATHOGENIC FUNGI

BACKGROUND OF THE INVENTION

Copending patent applications Ser. Nos. 07/803,289 and 07/803,294 filed on Dec. 4, 1991, concurrently herewith describe certain trifluoromethylsulfonylpyrroles useful as insecticidal and fungicidal agents, respectively. Copending patent application Ser. No. 07/804,260, filed Dec. 4, 1991 concurrently herewith describes the insecticidal, acaricidal and molluscicidal use of 1-(substituted)thioalkylpyrrole compounds.

Although certain arylpyrrole compounds have been described as antifungal agents, no pyrrole compounds having a (substituted)thioalkyl moiety on the pyrrole ring nitrogen atom have been so described.

SUMMARY OF THE INVENTION

The present invention provides a method for the prevention, control or amelioration of a disease caused by a phytopathogenic fungus which comprises contacting said fungus with a fungicidally effective amount of a 1-(substitued)thioalkylpyrrole compound of formula I

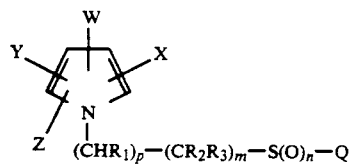

wherein

W is CN or $NO_2$;

X is halogen or phenyl optionally substituted with one to three $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, halogen, CN, $NO_2$, $CF_3$, $R_4CF_2B$, $R_5CO$ or $NR_6R_7$ groups;

Y is $CF_3$, halogen or phenyl optionally substituted with one to three $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, halogen, CN, $NO_2$, $CF_3$, $R_4CF_2B$, $R_5CO$ or $NR_6R_7$ groups;

Z is halogen or $CF_3$;

$R_1$ is hydrogen, $C_1$-$C_6$alkyl or $C_3$-$C_6$cycloalkyl;

$R_2$ and $R_3$ are each independently hydrogen, $C_1$-$C_6$alkyl or $C_3$-$C_6$cycloalkyl;

$R_4$ is hydrogen, fluorine, $CHF_2$, CHFCl or $CF_3$;

$R_5$ is $C_1$-$C_3$alkyl, $C_1$-$C_3$alkoxy or $NR_6R_7$;

$R_6$ is hydrogen or $C_1$-$C_3$alkyl;

$R_7$ is hydrogen, $C_1$-$C_3$alkyl or $R_8CO$;

$R_8$ is hydrogen or $C_1$-$C_3$alkyl;

B is $S(O)_q$ or O;

m, n, p and q are each independently an integer of 0, 1 or 2 with the proviso that the sum (p+m) must be greater than 0;

Q is

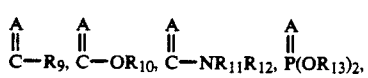

-continued

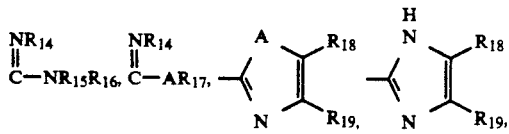

CN, $C_1$-$C_6$alkyl optionally substituted with one or more phenyl, CN or halogen groups or phenyl optionally substituted with one to three $C_1$-$C_3$alkyl, $C_1$-$C_3$alkoxy, halogen, CN, $NO_2$, $CF_3$ or $NR_{20}R_{21}$ groups;

A is O or S;

$R_9$ is $C_1$-$C_6$alkyl or phenyl;

$R_{10}$ is $C_1$-$C_6$alkyl;

$R_{11}$ and $R_{12}$ are each independently hydrogen, $C_1$-$C_6$alkyl or may be taken together with the atom to which they are attached to form a 5- to 7- membered ring;

$R_{13}$ is $C_1$-$C_4$alkyl;

$R_{14}$ is hydrogen, $C_1$-$C_4$alkyl or may be taken together with either $R_{15}$ or $R_{17}$ and the atoms to which they are attached to form a 5- to 7-membered ring optionally substituted with one or two $C_1$-$C_3$alkyl groups;

$R_{15}$ and $R_{16}$ are each independently hydrogen or $C_1$-$C_4$alkyl;

$R_{17}$ is $C_1$-$C_4$alkyl or when taken together with $R_{14}$ and the atoms to which they are attached may form a 5- to 7-membered ring optionally substituted with one or two $C_1$-$C_3$alkyl groups;

$R_{18}$ and $R_{19}$ are each independently hydrogen or $C_1$-$C_3$alkyl or when taken together may form a ring wherein $R_{18}R_{19}$ is represented by —CH=CH—CH=CH—;

$R_{20}$ and $R_{21}$ are each independently hydrogen or $C_1$-$C_3$alkyl and the acid addition salts therof.

There are also provided compositions useful for the control of the fungal causative agents of plant disease. And, further, a method is provided for the protection of crops, both growing and harvested, from infestation and disease caused by phytopathogenic fungi.

DETAILED DESCRIPTION OF THE INVENTION

Throughout time, agriculturalists have been seeking effective and efficient means of combatting fungi which cause harmful disease such as mildew, blight, blast, rust, rot and the like. Said diseases cause considerable economic damage to essential crops, particularly fruits, nuts and vegetables, when left unchecked. There is a long-felt need in the art for alternative, effective compounds and compositions useful for agricultural applications as fungicidal agents.

It is an object of the present invention to provide methods and compositions for the protection of agronomic crops, crop seed and tubers both growing and harvested, from the ravages of disease caused by phytopathogenic fungi.

The 1-(substituted)thioalkylpyrrole antifungal agents of the invention have the structural formula I

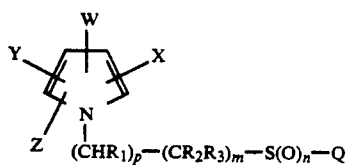

(I)

wherein W, X, Y, Z, $R_1$, $R_2$, $R_3$, m, n, p and Q are as described hereinabove. The term halogen, as used in the specification and claims, designates chlorine, fluorine, bromine and iodine. Acid addition salts are those known in the art such as hydrogen halides, hydrogen sulfates, sulfates, sulfonates and the like.

Preferred fungicidal agents of the invention are those having structure II

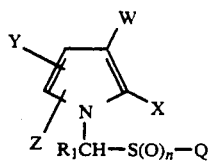

(II)

wherein W is CN, n is O and X, Y, Z, $R_1$ and Q are as described hereinabove.

Compounds of formula II which are particularly effective fungicidal agents are those wherein W is CN; X is halogen or phenyl optionally substituted with one to three halogen or $CF_3$ groups; Y and Z are each independently halogen; $R_1$ is hydrogen; n is O and Q is CN, phenyl optionally substituted with one to three halogen or $CF_3$ groups or

wherein A and $R_{13}$ are described hereinabove.

Certain 1-(substituted)thioalkylpyrrole compounds of formula I may be prepared by reacting a pyrrole compound of formula III with a suitable dithiocarbamate, thiocarbamate, thiophosphate or mercaptate alkali metal salt. A specific example of this reaction is illustrated in flow diagram I.

Flow Diagram I

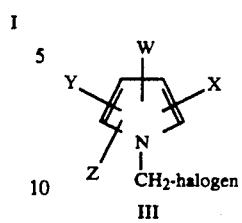 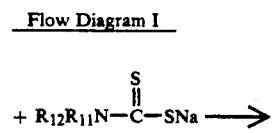

(III)

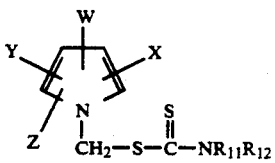

Moreover, certain compounds of formula I may be prepared by reacting the appropriate halomethyl thioether with a pyrrole compound of formula IV in the presence of a base. A representative example is shown in flow diagram II Flow Diagram II

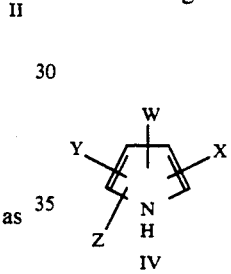 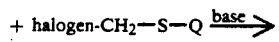

(IV)

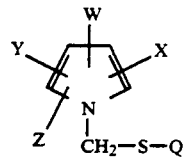

Compounds of formulas III and IV are described in U.S. Pat. No. 5,010,098 and copending patent applications Ser. No. 634,288 filed on Dec. 26, 1990, U.S. Pat. No. 5,194,630 and Ser. No. 07/795,407 filed on Nov. 20, 1991, U.S. Pat. No. 5,204,332 and incorporated herein by reference thereto.

Other compounds of formula I may be prepared by reacting a 1-(halomethyl)pyrrole compound of formula III with a suitable thiourea reagent. In this reaction scheme, the product may be isolated as its acid addition salt. The free base may be obtained using standard procedures such as treatment with excess aqueous base and filtration or extraction of the desired product with a suitable solvent. An illustrative example is shown in flow diagram III.

Flow Diagram III

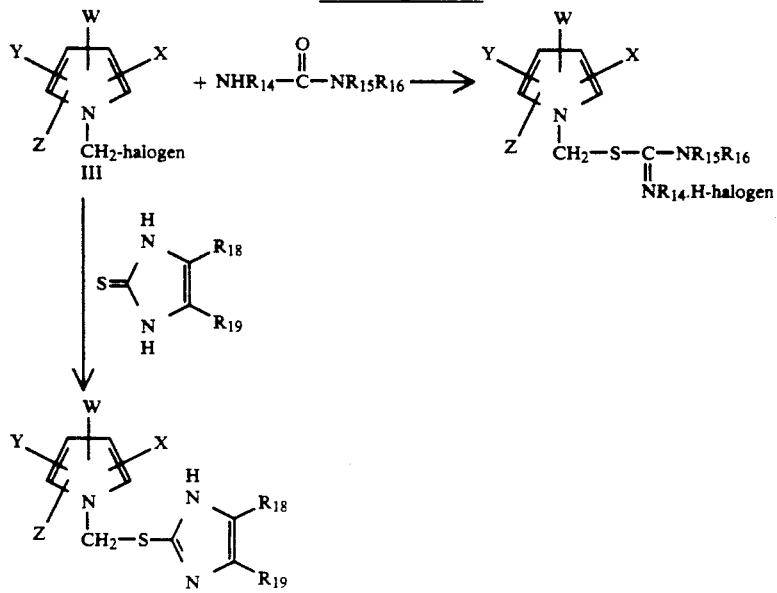

Further compounds of formula I may be prepared by reacting a pyrrole compound of formula IV with a halomethyl compound of formula V wherein $R_1$ is defined hereinabove in the presence of a base such as an alkali metal alkoxide to form the pyrrole intermediate of formula VI. The formula VI intermediate may then be halogenated using conventional halogenating reagents such as N-bromosuccinimide (NBS) to give the desired 1-(haloalkyl)pyrrole second intermediate of formula VII which may then be reacted with an alkali metal thiocarbamate, dithiocarbamate, mercaptate, thiophosphate or the like to yield the 1-(substituted)thioalkylpyrrole product as shown in flow diagram IV.

Flow Diagram IV

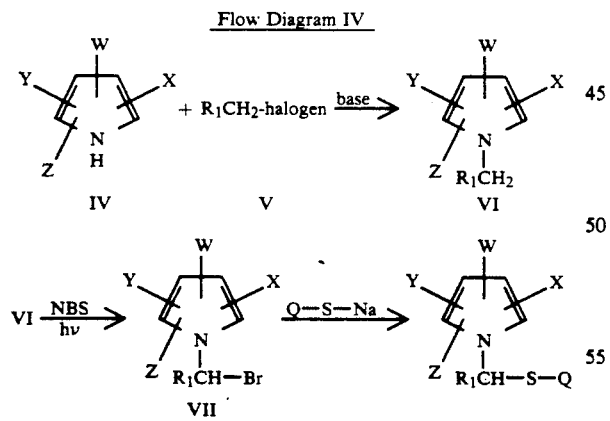

Yet further pyrrole compounds of the invention may be prepared by reacting the formula IV pyrrole with an epoxide of formula VIII in the presence of a base to give the β-hydroxy pyrrole intermediate of formula IX which can then be converted to the corresponding tosylate of formula X by reaction with p-toluenesulfonyl chloride (tsCl) in the presence of an organic base such as pyridine. The tosylate intermediate of formula X may then be reacted with an alkali metal thiocarbamate, dithiocarbamate, mercaptate, thiophosphate or the like to yield the desired 1-(substituted)thioalkylpyrrole product as shown in flow diagram V.

Flow Diagram V

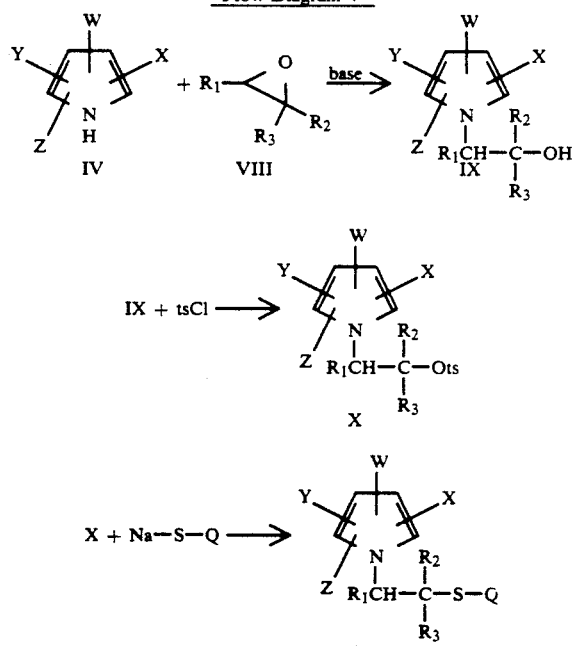

Examples are provided below for the purpose of illustration. The examples utilize the above reaction schemes and also provide further means for preparing even more compounds of the invention which are not specifically described hereinabove.

The 1-(substituted)thioalkylpyrrole compounds of the present invention are effective for controlling phytopathogenic fungi which are causative agents for a variety of destructive diseases. Said pyrroles are also effective for protecting growing or harvested crops, seed and tubers from infection by said diseases.

The effective amount of the 1-(substituted)thioalkyl pyrroles of the invention will vary with the virility of the target fungus, the environment of the treatment and the like. In practice, generally about 20 ppm to 1,000 ppm, preferably about 50 ppm to 500 ppm of the formula I thioalkylpyrrole dispersed in a liquid carrier when applied to the plant, seed or tuber, or to the soil or water in which they are growing, is effective to protect the plant, seed or tuber from fungal infestation and disease caused thereby.

The formula I fungicidal agents may be formulated as solutions, suspensions, emulsifiable contrates, flowable concentrates, wettable powders and the like which are diluted with water or other suitable polar solvents, generally in situ, and then applied as a dilute spray.

Said formula I agents may also be formulated in dry compacted granules, dusts, dust concentrates, suspension concentrates, microemulsions and the like. All compositions which lend themselves to seed, soil, water or foliage applications and provide effective plant protection are suitable. Said compositions include the formula I compound admixed with an inert liquid or solid diluent.

For example, wettable powders, dusts, and dust concentrate formulations can be prepared by grinding and blending together about 25% to 85% by weight of the formula I thioalkylpyrrole and about 75% to 15% by weight of a solid diluent such as bentonite, diatomaceous earth, kaolin, attapulgite, or the like, 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethyleneglycol, and 54% by weight of water.

A typical emulsifiable concentrate can be prepared by dissolving about 15% to 70% by weight of the active ingredient in about 85% to 30% by weight of a solvent such as isophorone, toluene, butyl cellosolve, methyl acetate, propylene glycol monomethyl ether, or the like and dispersing therein about 1% to 5% by weight of a nonionic surfactant such as an alkylphenoxy polyethoxy alcohol.

Application of the material is made by adding a predetermined quantity of formulated product, such as described above, to the desired volume of water or other suitable solvent, alone or in combination with other agronomic chemicals for simultaneous use.

Advantageously, the compounds of the invention may be used effectively in conjunction with, or in combination with, other biological chemicals, including, but not limited to, probenazole, anilazine, benalaxyl, phosdiphen, capatafol, carboxin, chlorothanil, dichlorophen, diethofencarb, dithianon, ethoxyquin, fenfuram, ferbam, flusulfamide, iprobenfos, mancozeb, myclobutanil, oxadixyl, prochloraz, and the like.

Where compositions of the invention are to be employed in combination treatments with other pesticidal agents, the composition may be applied as an admixture of the components as described herinabove or may be applied sequentially.

For a more clear understanding of the invention, specific detailed examples of it are set forth below. These examples are merely illustrative, and are not to be understood as limiting the scope and underlying principles of the invention in any way.

Unless otherwise noted, all parts are parts by weight. H¹NMR and C¹³NMR designate proton nuclear magnetic resonance and carbon 13 nuclear magnetic resonance, respectively.

EXAMPLE 1

Preparation of
4-bromo-2-(p-chlorophenyl)-1-[(imidazol-2-ylthio)methyl]-5-trifluoromethylpyrrole-3-carbonitrile hydrobromide

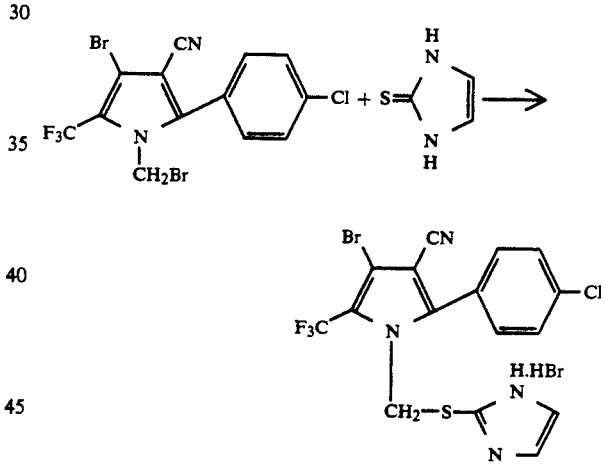

A mixture of 4-bromo-1-(bromomethyl)-2-(p-chlorophenyl)-5-(trifluoromethyl)pyrrole-3-carbonitrile (0.88g, 0.002 mol) and 4-imidazoline-2-thione (0.23g, 0.002 mol) in isopropanol is heated at reflux temperature for 3 hours, cooled to room temperature and filtered. The filtercake is washed with isopropanol and air-dried to give the title product as a white solid, 0.81 g (75% yield), mp 221°-223° C.(dec).

EXAMPLES 2-20

Preparation of 1-[(substituted)thiomethylpyrroles

Using the procedure described in Example 1 and employing the appropriately substituted 1-(halomethyl)pyrrole substrate and a suitable thiourea reagent, the following 1-[(substituted)thiomethyl]pyrrole compounds shown in Table I are obtained.

TABLE I

Structure: pyrrole ring with substituents Z, Y, W, X and N-CH₂-S-Q·acid salt

| Ex. No. | Z | Y | W | X | Q | acid salt | mp °C. |
|---|---|---|---|---|---|---|---|
| 2 | CF₃ | Cl | CN | 4-Cl-phenyl | C(=NCH₃)-N(CH₃)H (N,N'-dimethylacetamidine) | HCl | 141–144 |
| 3 | CF₃ | Cl | CN | 4-Cl-phenyl | C(=NH)-NH₂ (acetamidine) | HCl | 210–213 |
| 4 | CF₃ | Cl | CN | 4-Cl-phenyl | 4,5-dihydro-1H-imidazol-2-yl | HCl | 189–191 |
| 5 | CF₃ | Cl | CN | 4-Cl-phenyl | 1,4,5,6-tetrahydropyrimidin-2-yl | HCl | 227–229 |
| 6 | CF₃ | Br | CN | 4-Cl-phenyl | benzoxazol-2-yl | free base | 135–137 |
| 7 | CF₃ | Br | CN | 4-Cl-phenyl | 4,5-dihydro-1H-imidazol-2-yl | HBr | 228–230 |
| 8 | CF₃ | Br | CN | 4-Cl-phenyl | 1,4,5,6-tetrahydropyrimidin-2-yl | HBr | >225 |
| 9 | CF₃ | Br | CN | 4-Cl-phenyl | benzimidazol-2-yl | HBr | 215–218 (dec) |
| 10 | CF₃ | Br | CN | 4-Cl-phenyl | 5,5-dimethyl-1,4,5,6-tetrahydropyrimidin-2-yl | HBr | 224–227 |
| 11 | CF₃ | Br | CN | 4-Cl-phenyl | 1,4,5,6,7-pentahydro-1,3-diazepine-2-thione-yl (7-membered ring with N, N-H, C=S) | HBr | 232–234 (dec) |

TABLE I-continued

[Structure: pyrrole ring with Y at position 4, W at position 3, Z at position 5, X at position 2, N-H substituted with CH₂—S—Q·acid salt]

| Ex. No. | Z | Y | W | X | Q | acid salt | mp °C. |
|---|---|---|---|---|---|---|---|
| 12 | CF₃ | Br | CN | 4-Cl-C₆H₄ | CH₃CH₂N=C(CH₃)–NHCH₂CH₃ | HBr | 128–130 |
| 13 | Br | Br | CN | Br | 2-(tetrahydropyrimidinyl) | HBr | 215 (dec) |
| 14 | Br | Br | CN | Br | CH₃N=C(CH₃)–NHCH₃ | HCl | 216 |
| 15 | Cl | Cl | CN | 3,4-diCl-C₆H₃ | CH₃N=C(CH₃)–NHCH₃ | HCl | 180–184 |
| 16 | CF₃ | Br | CN | 4-Cl-C₆H₄ | 2-methyl-dihydrothiazine | free base | 124.5–125.5 |
| 17 | CF₃ | CF₃ | Br | 3,4-diCl-C₆H₃ | 2-(tetrahydropyrimidinyl) | HCl | 225–228 (dec) |
| 18 | CF₃ | CF₃ | Br | 3,4-diCl-C₆H₃ | HN=C(CH₃)–NH₂ | HCl | 221 (dec) |
| 19 | Cl | CN | Cl | 3,4-diCl-C₆H₃ | CH₃N=C(CH₃)–NHCH₃ | HCl | 194–197 |
| 20 | Br | Br | CN | Br | HN=C(CH₃)–NH₂ | HCl | 225 (dec) |

Ex. No. designates Example Number

EXAMPLE 21

Preparation of [3-Chloro-5-(p-chlorophenyl)-4-cyano-2-(trifluoromethyl)pyrrole-1-yl]dimethyldithiocarbamic acid, methyl ester

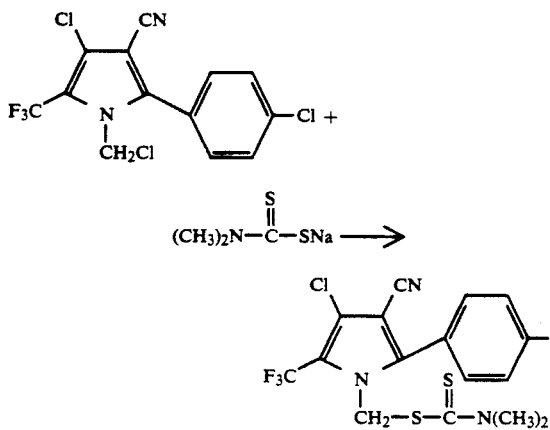

A mixture of 4-chloro-1-(chloromethyl)-2-(p-chlorophenyl)-5-(trifluoromethyl)pyrrole-3-carbonitrile (0.7 g, 0.002 mol) and dimethyldithiocarbamic acid, sodium salt (0.57 g, 0.004 mol) in dimethyl formamide is heated at 50°–55° for 30 minutes, cooled to room temperature and poured into water. The resultant mixture is extracted with ethyl acetate. The combined extracts are washed with a saturated sodium chloride give an orange oil residue. The residue is mixed with hot hexane, cooled and filtered to give an orange solid filtercake. Recrystallization of the solid from isopropanol gives the title product as a tan crystaline solid, 0.7 g (80% yield), mp 129°–131° C.

EXAMPLES 22-43

Preparation of [(substituted pyrrole-1-yl)dithiocarbamate, thiocarbamate and thiophosphate methyl esters and thioalkyl derivatives Using the procedure described in Example 21 and employing the appropriately substituted 1-halo methylpyrrole and the sodium salt of the desired dithiocarbamate, thiocarbamate, thiophosphate or mercaptate reagent the following compounds shown in Table II are obtained.

TABLE II

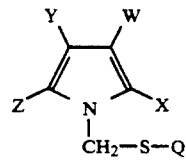

| Ex. No. | Z | Y | W | X | Q | mp °C. |
|---|---|---|---|---|---|---|
| 22 | CF$_3$ | Cl | CN | Cl—C$_6$H$_4$— | (CH$_3$)$_2$CHOC(=S)— | 94–95 |
| 23 | CF$_3$ | Cl | CN | Cl—C$_6$H$_4$— | CH$_3$CH$_2$OC(=S)— | (oil) |
| 24 | CF$_3$ | Br | CN | Cl—C$_6$H$_4$— | (CH$_3$)$_2$NNC(=S)— | 125–128 |
| 25 | CF$_3$ | Br | CN | Cl—C$_6$H$_4$— | CH$_3$ | |
| 26 | CF$_3$ | Br | CN | Cl—C$_6$H$_4$— | (CH$_3$CH$_2$)$_2$NC(=S)— | 101–103 |
| 27 | CF$_3$ | Br | CN | Cl—C$_6$H$_4$— | [(CH$_3$)$_2$CHO]$_2$P(=S)— | 108–110 |

TABLE II-continued

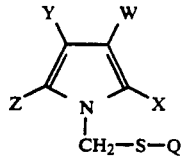

| Ex. No. | Z | Y | W | X | Q | mp °C. |
|---|---|---|---|---|---|---|
| 28 | Cl | Cl | CN | 3,4-dichlorophenyl | CH₃CH₂OC(=S)— | 82–85 |
| 29 | CF₃ | Br | CN | 4-chlorophenyl | CH₃CH₂OC(=S)— | 85–86 |
| 30 | CF₃ | Br | CN | 4-chlorophenyl | (CH₃)₂CHOC(=S)— | 120–121.5 |
| 31 | Br | Br | CN | Br | (CH₃)₂NC(=S)— | 170–172 |
| 32 | Cl | Cl | CN | 3,4-dichlorophenyl | (CH₃)₂NC(=S)— | 194–197 |
| 33 | CF₃ | CF₃ | Br | 3,4-dichlorophenyl | (CH₃)₂NC(=S)— | 128–129 |
| 34 | Br | Br | CN | Br | CH₃C(=O) | 135–137 |
| 35 | CF₃ | CF₃ | Br | 3,4-dichlorophenyl | CH₃CH₂OC(=S)— | (oil) |
| 36 | Cl | CN | Cl | 3,4-dichlorophenyl | (CH₃)₂NC(=S)— | 120–123 |
| 37 | Cl | CN | Cl | 3,4-dichlorophenyl | CH₃CH₂OC(=S)— | 100–105 |
| 38 | Br | Br | CN | Br | CN | 168–170 |
| 39 | Br | Br | CN | C₆H₅CH₂S— | C₆H₅CH₂— | 50–53 |

TABLE II-continued

![structure]

| Ex. No. | Z | Y | W | X | Q | mp °C. |
|---|---|---|---|---|---|---|
| 40 | Br | Br | CN | Br | —CH₂—(phenyl) | 106–110.5 |
| 41 | CF₃ | Br | CN | 4-Cl-C₆H₄— | pyrrolidine-N-C(=S)— | 106–110 |
| 42 | CF₃ | Br | CN | 4-Cl-C₆H₄— | CN | 95–97 |
| 43 | Br | Br | CN | CH₃S— | CH₃— | 110–111 |

Ex. No. designates Example Number

EXAMPLE 44

Preparation of 4,5-dibromo-1[(methylthio)methyl]-2-(α,α,α-trifluoro-p-tolyl)pyrrole-3-carbonitrile

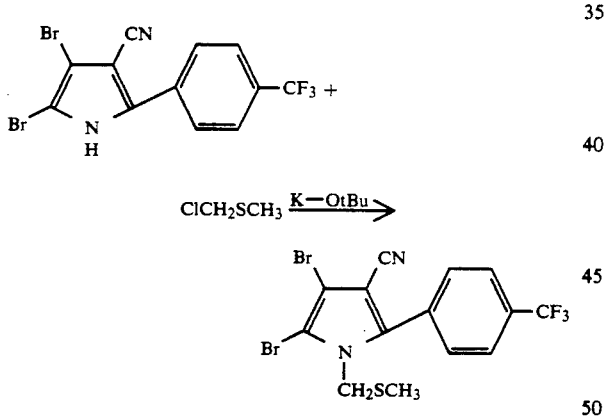

A solution of 4,5-dibromo-2-(α,α,α-trifluoro-p-tolyl)-pyrrole-3-carbonitrile (0.56 g, 1.42 mmol) in dry tetrahydrofuran, under nitrogen, is treated portion-wise with potassium t-butoxide (0.21 g, 1.81 mmol), stirred at 25° C. for ¼ hour, treated dropwise with chloromethyl methyl thioether (0.18 g, 1.81 mmol), stirred at room temperature for 16 hours, heated at 49°–60° C. until reaction is complete by thin layer chromatography. The reaction mixture is diluted with water and ether. The phases are separated and the organic layer is dried over MgSO₄ and concentrated in vacuo to give a black oil residue. The residue is flash chromatographed (silica/ 100:100:1 ether:petroleum ether:ethyl acetate) to give the title product as a red solid, mp 140°–145° C., identified by H¹NMR and mass spectral analyses.

EXAMPLE 45

Preparation of 4,5-dibromo-1[(phenylthio)methyl]-2-(α,α,α-trifluoro-p-tolyl)pyrrole-3-carbonitrile

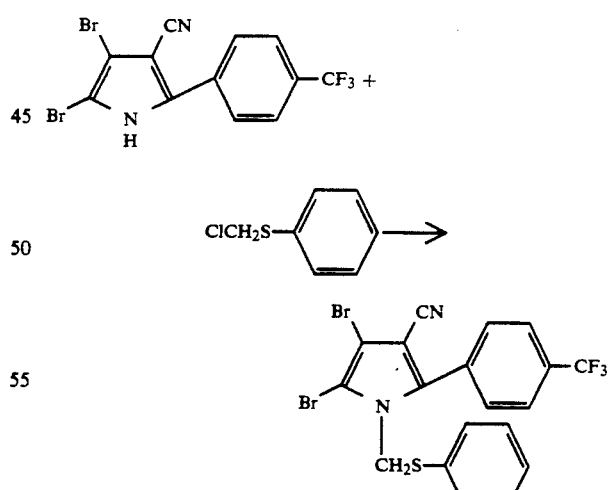

Following the procedure described in Example 44, above, and substituting chloromethyl phenyl thioether as the alkylating reagent, the title product is obtained as a red oil, bp >200° C./0.7 mmHg, identified by H¹NMR, C¹³NMR and mass spectral analyses.

EXAMPLE 46

Preparation of 4-bromo-2-(p-chlorophenyl)-1-[(phenylsulfonyl)methyl]-5-trifluoromethyl)pyrrole-3-carbonitrile

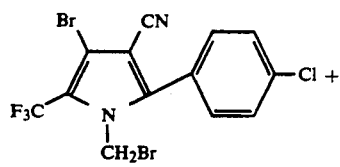

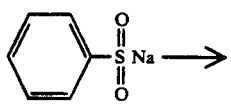

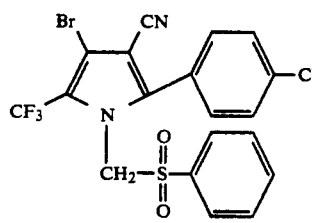

A stirred solution of 4-bromo-1-(bromomethyl)-2-(p-chlorophenyl)-5-(trifluoromethyl)pyrrole-3-carbonitrile (0.65 g, 1.5 mmol) in dry dimethyl formamide is treated with sodium benzylsulfonate (0.485 g, 3.0 mmol), heated at 70° C. for 3 hours, cooled to room temperature and diluted with a mixture of water and ethyl acetate. The organic phase is separated, dried over MgSO$_4$ and concentrated in vacuo to give a yellow oil residue. Column chromatography (silica gel/4:1 hexanes:ethyl acetate) gives the title product as a white solid, mp 165°-166.5° C., identified by HINMR and mass spectral analyses.

EXAMPLE 47

Evaluation of In Vivo Fungicidal Activity of Test Compounds

Test compounds are dissolved in acetone and diluted with deionized water containing about 0.05% TWEEN 20 ®, a polyoxyethylene sorbitan monolaurate surfactant manufactured by Atlas Chemical Industries, to give a concentration of 400 ppm. Subsequent dilutions are made with an 0.05% aqueous solution of TWEEN 20 ®.

Host plants are sprayed with test solution, dried and inoculated with fungi. When disease symptom development is optimal, the plants are rated for disease control according to the rating scale shown below. Each test contains inoculated treated plants, inoculated untreated plants and a reference standard.

| Symbol | Disease | Pathogen |
|---|---|---|
| AS | Apple Scab | *Venturia inaequalis* |
| GDM | Grape Downy Mildew | *Plasmopara viticola* |
| SBC | Sugarbeet Cercospora | *Cercospora beticola* |
| WLR | Wheat Leaf Rrust | *Puccinia recondita, tritici* |
| WPM | Wheat Powdery Mildew | *Erysiphe graminis, tritici* |

| Rating Scale | |
|---|---|
| Rating | Range % Control |
| 0 | 0 |
| 1 | 1-19 |
| 2 | 20-29 |
| 3 | 30-39 |
| 4 | 40-59 |
| 5 | 60-74 |
| 6 | 75-89 |
| 7 | 90-96 |
| 8 | 97-99 |
| 9 | 100 |
| — | no evaluation |

When more than one test is run, the data are averaged. The data obtained are shown in Table III.

TABLE III

Evaluation of Test Compounds For The Control Of Plant Pathogenic Fungi

| Compound | Rate (ppm) | AS | GDM | SBC | WLR | WPM |
|---|---|---|---|---|---|---|
| 4,5-dibromo-1-[(phenyl-thio)methyl]-2-(alpha,alpha,alpha-trifluoro-p-tolyl)pyrrole-3-carbonitrile | 25<br>100<br>400 | —<br>—<br>0 | —<br>—<br>0 | 6.0<br>7.0<br>7.5 | —<br>—<br>6.0 | —<br>—<br>1.0 |
| 1-[(cyanothio)methyl]-2,4,5-tribromopyrrole-3-carbonitrile | 400 | 2.0 | 3.0 | 0 | 5.0 | 0 |
| O,O-diisopropyl S-(2,3,5-tribromo-4-cyano-pyrrole-1-yl)methyl ester phosphorodithioic acid | 25<br>100<br>400 | —<br>—<br>0 | —<br>—<br>0 | —<br>—<br>0 | —<br>—<br>0 | 0<br>4.0<br>7.0 |

EXAMPLE 48

Evaluation of In Vitro Fungicidal Activity of Test Compounds

Test compounds are dissolved in acetone, diluted with sterile, deionized water and mixed with a partially cooled, autoclaved, chemically defined agar medium. This mixture is poured into several 100 mm×15 mm sterile plastic plates and allowed to solidify. The surface of each plate is inoculated with a single disc of mycelium and agar cut with an 8 mm diameter cork borer from actively growing cultures of assay fungi on a chemically defined agar medium. The plates are incubated at room temperature. Growth inhibition is determined when the mycelial growth on unamended control media has reached the edge of the petri plates. The time interval varies depending on the growth rate of the fungus; two days for *Pythium ultimum* (pyth) and *Rhizoctonia solani* (Rhiz), five days for *Botrytis cinerea* (Betry), and 7-10 days for *Pseudocercosporella herpotrichoides* (Pseudo). Each colony diameter is measured and compared with the untreated control and the percent inhibition is calculated as follows:

$$\% \text{ Mycelial growth inhibition} = \frac{\text{Growth of untreated control (mm) minus the Growth of treatment (mm)}}{\text{Growth of untreated control (mm)}} \times 100$$

Each test includes a solvent blank consisting of the formulation without a test compound in addition to the untreated control.

Assay fungi include the plant pathogens, *Pythium ultimum* (Pyth) and *Rhizoctonia solani* (Rhiz).

When more than one test is run the data are averaged. The data obtained are shown in Table IV.

TABLE IV
Evaluation Of Test Compounds For The Control Of The Mycelial Growth Of Fungi

| Compound Name | Rate (ppm) | % Growth Inhibition Pyth | Rhiz |
|---|---|---|---|
| 4,5-dibromo-1-[(phenylthio)-methyl]-2-(alpha,alpha,alpha-trifluoro-p-tolyl)pyrrole-3-carbonitrile | 1 | 0 | 0 |
|  | 10 | 7.0 | 3.5 |
|  | 25 | 4.5 | 2.0 |
| 1-[(cyanothio)methyl]-2,4,5-tribromopyrrole-3-carbonitrile | 1 | 1.5 | 1.5 |
|  | 10 | 4 | 3.5 |
|  | 25 | 4.5 | 5.8 |

What is claimed is:

1. A method for the prevention, control or amelioration of a disease caused by a phytopathogenic fungus which comprises contacting said fungus with a fungicidally effective amount of a compound having the structure

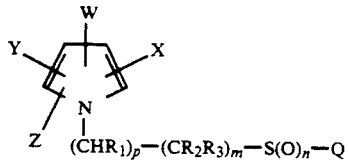

wherein
W is CN or $NO_2$;
X is halogen or phenyl optionally substituted with one to three $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, halogen, CN, $NO_2$, $CF_3$, $R_4CF_2B$, $R_5CO$ or $NR_6R_7$ groups;
Y is $CF_3$, halogen or phenyl optionally substituted with one to three $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, halogen, CN, $NO_2$, $CF_3$, $R_4CF_2B$, $R_5CO$ or $NR_6R_7$ groups;
Z is halogen or $CF_3$;
$R_1$ is hydrogen, $C_1$-$C_6$alkyl or $C_3$-$C_6$cycloalkyl;
$R_2$ and $R_3$ are each independently hydrogen, $C_1$-$C_6$alkyl or $C_3$-$C_6$cycloalkyl;
$R_4$ is hydrogen, fluorine, $CHF_2$, CHFCl or $CF_3$;
$R_5$ is $C_1$-$C_3$alkyl, $C_1$-$C_3$alkoxy or $NR_6R_7$;
$R_6$ is hydrogen or $C_1$-$C_3$alkyl;
$R_7$ is hydrogen, $C_1$-$C_3$ alkyl or $R_8CO$;
$R_8$ is hydrogen or $C_1$-$C_3$alkyl;
B is $S(O)_q$ or O;
m, n, p and q are each independently an integer of 0, 1 or 2 with the proviso that the sum (p+m) must be greater than 0;

Q is

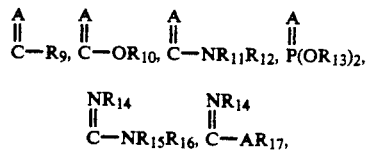

CN, $C_1$-$C_6$alkyl optionally substituted with one or more phenyl, CN or halogen groups or phenyl optionally substituted with one to three $C_1$-$C_3$alkyl, $C_1$-$C_3$alkoxy, halogen, CN, $NO_2$, $CF_3$ or $NR_{20}R_{21}$ groups;
A is O or S;
$R_9$ is $C_1$-$C_6$alkyl or phenyl;
$R_{10}$ is $C_1$-$C_6$alkyl;
$R_{11}$ and $R_{12}$ are each independently hydrogen or $C_1$-$C_6$alkyl;
$R_{13}$ is $C_1$-$C_4$alkyl;
$R_{14}$ is hydrogen or $C_1$-$C_4$alkyl;
$R_{15}$ and $R_{16}$ are each independently hydrogen or $C_1$-$C_4$alkyl;
$R_{17}$ is $C_1$-$C_4$alkyl;
$R_{20}$ and $R_{21}$ are each independently hydrogen or $C_1$-$C_3$alkyl and
the acid addition salts thereof.

2. The method according to claim 1 wherein the compound has the structure

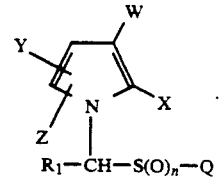

3. The method according to claim 2 wherein W is CN; X is halogen or phenyl optionally substituted with one to three halogen or $CF_3$ groups; Y and Z are each independently halogen; $R_1$ is hydrogen; n is 0 and Q is CN, phenyl optionally substituted with one to three halogen or $CF_3$ groups or

4. The method according to claim 3 wherein the compound is 4,5-dibromo-1-[(phenyltho)methyl]-2-α,α,α-trifluoro-p-tolyl)pyrrole-3-carbonitrile.

5. The method according to claim 3 wherein the compound is 1-[(cyanothio)methyl]2,4,5-tribromopyrrole-3-carbonitrile.

6. The method according to claim 3 wherein the compound is O,O-diisopropyl S-(2,3,5-tribromo-4-cyanopyrrol-1-yl)methyl ester phosphorodithioc acid.

* * * * *